United States Patent
Gardlik et al.

(10) Patent No.: US 8,002,850 B2
(45) Date of Patent: Aug. 23, 2011

(54) POWDERED HAIR COLORING AND BLEACHING COMPOSITIONS

(75) Inventors: John Michael Gardlik, Cincinnati, OH (US); Jeffrey Allen Bowles, Hamilton, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/950,384

(22) Filed: Nov. 19, 2010

(65) Prior Publication Data

US 2011/0119840 A1    May 26, 2011

(51) Int. Cl.
*A61Q 5/10* (2006.01)

(52) U.S. Cl. ............. 8/405; 8/524; 8/552; 8/557; 8/620; 8/101; 8/111

(58) Field of Classification Search ............. 8/405, 524, 8/552, 557, 620, 101, 111
See application file for complete search history.

(56) References Cited

U.S. PATENT DOCUMENTS

| 4,808,189 | A |   | 2/1989 | Oishi |       |
|-----------|---|---|--------|-------|-------|
| 5,769,901 | A | * | 6/1998 | Fishman | 8/406 |
| 5,961,665 | A |   | 10/1999 | Fishman |     |
| 6,190,421 | B1 |  | 2/2001 | Rondeau |      |
| 6,488,918 | B2 |  | 12/2002 | Hess |         |
| 7,204,861 | B2 |  | 4/2007 | Marsh |        |

FOREIGN PATENT DOCUMENTS

| EP | 572768 | 7/1997 |
| JP | 2006273759 | 10/2006 |

* cited by examiner

*Primary Examiner* — Eisa B Elhilo
(74) *Attorney, Agent, or Firm* — Laura R. Grunzinger

(57) ABSTRACT

Powder hair coloring or bleaching composition comprising: a) at least one solid source of carbonate ions, carbamate ions, hydrogencarbonate ions, or mixtures thereof; b) at least one solid source of oxidizing agent; c) at least one solid source of ammonium ions; and d) a crosslinked carboxylic acid polymer thickener having a particle size of no more than about 10 microns in an amount which, upon admixture of the powder composition with water to provide a concentration of from about 1% to about 3%, provides the dispersed composition a viscosity of from about 10000 mPas to about 20000 mPas when measured at 0.5 rpm using Brookfield viscometer spindle S52, and a pH of from about 8.5 to about 9.4.

12 Claims, No Drawings

POWDERED HAIR COLORING AND BLEACHING COMPOSITIONS

CROSS REFERENCE TO RELATED APPLICATION(S)

This application claims the benefit of PCT Application No. PCT/US2009/065,597 filed on Nov. 24, 2009.

FIELD OF THE INVENTION

The present invention relates to powdered hair coloring and bleaching compositions, which are prepared for use by the consumer by addition of water.

BACKGROUND OF THE INVENTION

A majority of current retail oxidative hair colorant products are based on a two-, three-, or four-component system in liquid form consisting of 1) a developer including water and hydrogen peroxide, 2) a tint base including water, oxidative dye precursors and alkalizing agent, and optionally 3) a further solvent-containing component for mixing with 1) and 2), and optionally 4) a post treatment hair conditioner. The packaging is complicated and shipping costs are substantial due to moving the relatively large volume of materials, especially water and solvent. Powdered product forms, which are prepared for use by the consumer by addition of water, minimize the impact of these 2 issues, and thus provide environmentally friendly products at lower cost.

Powdered hair coloring and bleaching compositions have been known in the art, however, the interest for development in this product form has been relatively modest, compared to the liquid product forms. This has left the performance of powdered form products not comparable to liquid form products. Typically observed underperforming areas of powdered form products include low lift and poor color uptake, resulting in ineffective dyeing of gray hair.

Further, due to the need to stabilize the dye precursors from reacting prior to mixing with water, absent means for stabilizing the dye precursors, the selection of dye precursors is limited to those available in sulfate or hydrochloride salt forms, thereby limiting the variety of shades. Suggestions have been made to stabilize and/or coat one of more of the components in the product, however, such treatment adds to cost, and thus is unfavorable for this product form which is typically positioned as an environmentally friendly lower cost product.

Still further, in this product form the inevitable generation of ammonia occurs when the product is mixed with water and the alkali and source of ammonia react. Such ammonia odor makes the preparation process for this product form very unpleasant.

Based on the foregoing, there is a need to provide powdered hair coloring and bleaching compositions which provide satisfactory lift and color uptake to the extent they can be used for gray hair, have the potential of providing a broader variety of shades, and provide less damage to the hair, while being easy to prepare and olfactory pleasant upon use when mixed with water, and having sufficient shelf stability.

None of the existing art provides all of the advantages and benefits of the present invention.

SUMMARY OF THE INVENTION

The present invention is directed to a powder hair coloring or bleaching composition comprising:

a) at least one solid source of carbonate ions, carbamate ions, hydrogencarbonate ions, or mixtures thereof;
b) at least one solid source of oxidizing agent;
c) at least one solid source of ammonium ions; and
d) a crosslinked carboxylic acid polymer thickener having a particle size of no more than about 10 microns in an amount which, upon admixture of the powder composition with water to provide a concentration of from about 1% to about 3%, provides the dispersed composition a viscosity of from about 10000 mPas to about 20000 mPas when measured at 0.5 rpm using Brookfield viscometer spindle S52, and a pH of from about 8.5 to about 9.4.

The present invention is also directed to a method of coloring or bleaching the hair comprising the steps of:
a) providing the composition mentioned above;
b) admixing the composition with a prescribed amount of water;
c) applying the dispersed composition to the hair;
d) allowing the dispersed composition to remain on the hair for from about 2 to about 60 minutes; and
e) rinsing the dispersed composition from the hair.

Upon application to the hair, the present invention provides satisfactory lift and color uptake to the extent they can be used for gray hair, have the potential of providing a broader variety of shades, and provide less damage to the hair, while being easy to prepare and olfactory pleasant upon use when mixed with water, and having sufficient shelf stability.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by volume of the total composition and presented as number of moles of component(s) in one litre of the composition, or "mol/l". When more than one composition is used during a treatment, the total volume to be considered is the total volume of all the compositions applied on the hair simultaneously (i.e. the volume found "on head") unless otherwise specified.

As used herein "composition" or "powder composition" relates to the powdered from of the present composition in which the product is offered to the consumer, and "dispersed composition" relates to the fluid composition provided by admixing the powder composition with prescribed amount of water.

Carbonate Ion Source

According to the present invention the compositions comprise a solid source of carbonate ions or carbamate ions or hydrogencarbonate ions or peroxymonocarbonate ions or any mixture thereof. The solid source of said ions herein are provided in the composition to provide a concentration of at least 0.2 mol/l upon admixture of the powder composition with water. The compositions of the present invention are designed to preferably provide from about 0.4 mol/l to about 2.0 mol/l, more preferably from about 0.5 mol/l to about 1.5 mol/l of the source of said ions, upon admixture of the powder composition with water.

Any solid source of these ions may be utilized. Suitable sources for use herein include sodium, potassium, lithium, calcium, magnesium, barium, ammonium salts of carbonate, carbamate and hydrogencarbonate ions and mixtures thereof such as sodium carbonate, sodium hydrogen carbonate, potassium carbonate, potassium hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred solid sources of carbonate ions, carbamate and hydrogencarbonate ions are sodium percarbonate, potassium percarbonate, calcium percarbonate, and mixtures thereof.

Oxidizing Agent

The compositions according to the present invention thus form peroxymonocarbonate ions. These ions are typically formed in-situ from the reaction between a source of hydrogen peroxide and carbonate ion. Consequently, the compositions according to the present invention comprise at least one source of an oxidizing agent. Preferred oxidizing agents for use herein are solid water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any solid oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and/or peroxidases may also be used. Mixtures of two or more such oxidizing agents can be used if desired. Preferred for use in the compositions according to the present invention are percarbonate (which may be used to provide a source of both oxidizing agent and carbonate ions), persulphates and combinations thereof.

According to the present invention the compositions are preferably designed to provide from about 0.1% to about 10% by weight, preferably from about 1% to about 7% by weight, and most preferably from about 2% to about 5% by weight of an oxidizing agent upon admixture of the powder composition with water.

Source of Ammonium Ions

According to the present invention the composition comprises at least one solid source of ammonium ions. Any solid source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium sulfate, ammonium carbonate, ammonium carbamate, ammonia and mixtures thereof. Preferably, the ammonium ions and carbonate ions are present in the composition at a weight ratio of from 3:1 to 1:10, preferably 2:1 to 1:5.

The compositions of the present invention are preferably designed to provide from about 0.1% to about 10% by weight, preferably from about 0.5% to about 5%, most preferably from about 1% to about 3% of ammonium ions upon admixture of the powder composition with water.

Crosslinked Carboxylic Acid Polymer Thickener

The aforementioned components of the present invention provide peroxycarbonate radicals upon dispersing the composition in water, which peroxycarbonate radical contributes to effective bleaching and coloring over a shortened period of time. This leads to improved lift and color uptake to the extent they can be used for gray hair. Further, by providing the dispersed composition to have a pH of from about 8.5 to about 9.4, preferably from about 9.0 to about 9.4, the concentration of peroxide can be reduced to mitigate hair fiber damage, while also reducing the emission of ammonia and reduce the odor therefrom. The resulting viscosity of the composition after admixing with water must be controlled to a certain range to allow the user to suitably apply to the hair. Upon admixture of the powder composition with water to provide a concentration from about 1% to about 3%, the target viscosity is from about 10000 mPas to about 20000 mPas, preferably from about 12000 mPas to about 18000 mPas when measured at 0.5 rpm using Brookfield viscometer spindle S52. One skilled in the art appreciates that the type and amount of thickener is not the only factor for the viscosity of the finally obtained composition, but also other components and interaction of components, such as addition of salts, and creation of lamellar structures and the like. Therefore, the remainder components must be taken into consideration for providing the desired viscosity. According to the present invention the composition comprises a buffering thickener meeting all of the following criteria:

(1) is compatible with the remaining solid components of the composition to provide stability over the shelf life;
(2) is readily dispersible upon admixing with water;
(3) provides appropriate viscosity upon admixing with water with mild mixing over a short period of time; and
(4) buffers the dispersed composition to the appropriate pH.

Surprisingly, it has now been found that crosslinked carboxylic acid polymers having a particle size of no more than about 10 microns, preferably from about 0.1 microns to about 7 microns, provide rapid and efficient thickening upon admixing with water, while providing the appropriate viscosity and targeted pH in the percarbonate systems of the present invention. Without being bound by theory, among the many high molecular weight and networked polymers available in the art, only selected polymers provide the rapid and efficient thickening without generating unacceptable clumps, and provide the desired viscosity without lengthy mixing that is not acceptable for this product form. Moreover, the crosslinked carboxylic acid polymer thickener of the present invention buffers the dispersed composition to the targeted pH, which pH is lower than other percarbonate systems known for use in powdered forms.

The cross-linked carboxylate acid polymers for use herein can be chosen, for example, from:
(i) cross-linked acrylic acid homopolymers;
(ii) copolymers of acrylic or (meth)acrylic acid and of C1-C30 alkyl acrylate or (meth)acrylate.

Preferable polymers are C10-C30 alkylacrylate crosspolymers. Commercially available crosslinked carboxylic acid polymers highly useful herein include the products sold under the names Carbopol ETD 2020, 10, 980, 981, 954, 2984, 5984 by the company Noveon.

The pH of the compositions can be determined by using either a Mettler Toledo MP220 or an MP225 pH equipment, fitted with a standard laboratory pH electrode. The equipment is calibrated before each use using standard calibration buffers and using standard calibration procedure.

Radical Scavenger

According to the present invention the compositions may further comprise a radical scavenger, preferably in an amount to provide from about 0.1% to about 10% by weight, more preferably from about 1% to about 7% by weight, upon admixture of the powder composition with water.

The radical scavengers useful herein are defined as a species that can react with a carbonate radical to convert the carbonate radical by a series of fast reactions to a less reactive species, i.e. a carbonate radical scavenger.

Whilst not being bound by theory, it is believed that the ability of the radical scavenger to convert the carbonate radical is dependant upon the energy of the charge transfer reaction as shown below:

Scavenger+$CO_3^{*-}$→Scavenger$^{*+}$+$CO_3^{2-}$ wherein the energy of the reaction is defined by:—

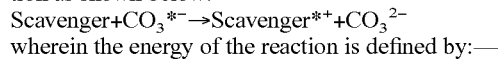

According to the present invention the composition do not comprise a radical scavenger having an energy of reaction of from about 0 kcal/mol to about 14 kcal/mol, preferably from about 1.5 kcal/mol to about 9 kcal/mol.

Useful radical scavengers herein include those of relatively low molecular weight which have the combination of hydroxyl and amine groups or combination of carboxyl and amine groups, such as alkanol amines and amino acids. Highly preferred radical scavengers herein are selected from the group consisting of glucosamine, glycine, glutamic acid, arginine, lysine, glutamine, histidine, serine, and mixtures thereof.

Additional Components

The compositions of the present invention may further comprise additional ingredients which include, but are not limited to, hair dyeing agents such as oxidative dye precursors, non-oxidative dyes, enzymes, surfactants, antioxidants, stabilizers such as erythorbic acid, chelants, perming actives, perfume, reducing agents (thiolactic acid), hair swelling agents and/or polymers. Some of these additional components are detailed hereafter.

Hair Dyes

The hair compositions of the present invention are preferably hair coloring compositions which comprise oxidative dyeing compositions. Such compositions comprise oxidative hair dye precursors (also known as primary intermediates or developers) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color. The choice of precursors and couplers will be determined by the color, shade and intensity of coloration that is desired. The precursors and couplers can be used herein, singly or in combination, to provide dyes having a variety of shades ranging from ash blonde to black.

Suitable precursors for use in the compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxy-ethyl)-amino]-ethanol (commonly known as N,N-bis(2-hydroxyethyl)-p-phenylenediamine); (2,5-diamino-phenyl)-methanol; 1-(2'-Hydroxyethyl)-2,5-diaminobenzene; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]propan-2-ol; $N^4,N^4$,2-trimethylbenzene-1,4-diamine; 2-methoxy-benzene-1,4-diamine; 1-(2,5-diaminophenyl)ethanol; 1-(2,5-diaminophenyl)ethane-1,2-diol; 2,3-dimethyl-benzene-1,4-diamine; N-(4-amino-3-hydroxy-phenyl)-acetamide; 2,6-diethylbenzene-1,4-diamine; 2,5-dimethylbenzene-1,4-diamine; 2-thien-2-ylbenzene-1,4-diamine; 2-thien-3-ylbenzene-1,4-diamine; 2-pyridin-3-ylbenzene-1,4-diamine; 1,1'-biphenyl-2,5-diamine; 2-(methoxymethyl)benzene-1,4-diamine; 2-(aminomethyl)benzene-1,4-diamine; 2-(2,5-diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxyethyl)-benzene-1,4-diamine; 3-[(4-aminophenyl)amino]propan-1-ol; 3-[(4-aminophenyl)-amino]propane-1,2-diol; N-{4-[(4-aminophenyl)amino]butyl}benzene-1,4-diamine; 2-[2-(2-{2-[(2,5-diaminophenyl)-oxy]ethoxy}ethoxy)ethoxy]benzene-1,4-diamine; 1,3-bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxyethylaminomethyl)benzene; 4-amino-2-methoxymethyl-phenol; 5-amino-2-hydroxy-benzoic acid; 1-(5-amino-2-hydroxyphenyl)-ethane-1,2-diol; 4-amino-2-(2-hydroxy-ethyl)-phenol; 4-amino-3-(hydroxymethyl)phenol; 4-amino-3-fluoro-phenol; 4-amino-2-(aminomethyl)-phenol; 4-amino-2-fluoro-phenol; 1-hydroxy-2,4-diaminobenzene; o-phenylenediamine derivatives such as: 3,4-Diaminobenzoic acid and salts thereof; o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraminopyrimidine); 1-methyl-1H-pyrazole-4,5-diamine; 2-(4,5-diamino-1H-pyrazol-1-yl)ethanol; $N^2,N^2$-dimethyl-pyridine-2,5-diamine; 2-[(3-amino-6-methoxypyridin-2-yl)amino]ethanol; 6-methoxy-$N^2$-methyl-pyridine-2,3-diamine; 2,5,6-triaminopyrimidin-4(1H)-one; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]- pyrimidine-3,7-diamine; 5,6,7-trimethylpyrazolo[1,5-a]pyrimidin-3-ylamine hydrochloride; 7-methylpyrazolo[1,5-a]pyrimidin-3-ylamine hydrochloride; 2,5,6,7-teramethyl-pyrazolo[1,5-a]pyrimidin-3-ylamine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidine-3,7-diamine hydrochloride; 4-hydroxy-2,5,6-triaminopyrimidine; 2,3-diamino-6,7-dihydropyrazolo[1,2-a]pyrazol-1(5H)-one dimethosulfonate 1-hydroxyethyl-4,5-diaminopyrazole; 2,5-diaminophenylethyl alcohol; and salts thereof.

Additional precursors are selected from the group consisting of N-(3-furylmethyl)benzene-1,4-diamine; N-thiophen-3-ylmethyl-benzene-1,4-diamine; N-(2-furylmethyl)benzene-1,4-diamine; N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-amino-phenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine; 2-[3-(3-amino-phenylamino)-propenyl]-benzene-1,4-diamine; 3-(2,5-diamino-phenyl)-N-ethyl-acrylamide; 2-thiazol-2-yl-benzene-1,4-diamine; 4-hydroxy-benzoic acid (2,5-diamino-benzylidene)-hydrazide; 3'-fluoro-biphenyl-2,5-diamine; 2-propenyl-benzene-1,4-diamine; 2'-chloro-biphenyl-2,5-diamine; N-thiophen-3-ylmethyl-benzene-1,4-diamine; N-(3-furylmethyl)benzene-1,4-diamine; 4'-methoxy-biphenyl-2,5-diamine; N-(4-amino-benzyl)-benzene-1,4-diamine; N-[4-amino-2-(2-hydroxy-ethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol hydrochloride; 4-amino-2-[(2-hydroxy-5-nitro-phenylamino)-methyl]-phenol hydrochloride; 4-amino-2-(pyridin-3-ylaminomethyl)-phenol; 5-cyclobutylamino-2-methyl-phenol; 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-$N^5$,$N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazol-4,5-diamine; 3-cyano-1-hexyl-1H-pyrazol-4,5-diamine; 1-butyl-3-cyano-1H-pyrazol-4,5-diamine; 3-cyano-1-(4-methoxybenzyl)-1H-pyrazol-4,5-diamine; 3-cyano-1-isopropyl-1H-pyrazol-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-(4-hydroxybutyl)-1H-pyrazol-4,5-diamine; 3-chloro-1-(pyridin-2-yl)-1H-pyrazole-4,5-diamine; 3-chloro-1-phenyl-1H-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxybenzyl)-3-(methylsulfonyl)-1H-pyrazole-4,5-diamine; 1-methyl-3-(methylsulfonyl)-1H-pyrazole-4,5-diamine; and salts thereof. In some embodiments, precursors include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; 2-(methoxymethyl)benzene-1,4-diamine; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-hydroxyethyl)-2,5-diaminobenzene; 1,3-bis(N-(2-hydroxyethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxymethyl-phenol; 1-(5-amino-2-hydroxy-phenyl)-ethane-1,2-diol; 4-amino-2-aminomethylphenol; 4-amino-1-hydroxy-2-(2'-hydroxyethylaminomethyl)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6-methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2$,$N^2$-dimethyl-pyridine-2,5-diamine; 4-Hydroxy-2,5,6-triaminopyrimidine; salts thereof; and mixtures thereof. In certain embodiments, precursors include: 2-methyl-benzene-1,4-diamine; 2-(methoxymethyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-aminophenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminotoluene; 2,5-diaminophenylethyl alcohol; salts thereof; and mixtures thereof.

Suitable couplers for use in the compositions described herein include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 2-isopropyl-5-methylphenol; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-chloro-2-methylbenzene-1,3-diol; 4,6-dichlorobenzene-1,3-diol; 2,3-dihydroxy-[1,4]naphthoquinone; and 1-Acetoxy-2-methylnaphthalene; m-phenylenediamines such as: 2,4-diaminophenol; benzene-1,3-diamine; 2-(2,4-diamino-phenoxy)-ethanol; 2-[(3-amino-phenyl)-(2-hydroxy-ethyl)-amino]-ethanol; 2-methyl-benzene-1,3-diamine; 2-[[2-(2,4- diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenylamino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenylamino]-ethanol; 3-(2,4-diamino-phenoxy)-propan-1-ol; N-[3-(dimethylamino)phenyl]urea; 4-methoxy-6-methyl-benzene-1,3-diamine; 4-fluoro-6-methylbenzene-1,3-diamine; 2-({3-[(2-hydroxyethyl)amino]-4,6-dimethoxyphenyl}-amino)ethanol; 3-(2,4-diaminophenoxy)-propane-1,2-diol; 2-[2-amino-4-(methylamino)-phenoxy]ethanol; 2-[(5-amino-2-ethoxy-phenyl)-(2-hydroxy-ethyl)-amino]-ethanol; 2-[(3-aminophenyl)amino]ethanol; 2,4-Diamino-5-(2'-hydroxyethyloxy)toluene; N,N-Dimethyl-3-ureidoaniline; N-(2-aminoethyl)benzene-1,3-diamine; 4-{[(2,4-diamino-phenyl)oxy]methoxy}-benzene-1,3-diamine; 1-methyl-2,6-bis(2-hydroxyethylamino)benzene; and 2,4-dimethoxyben-zene-1,3-diamine; 1,3-bis-(2,4-diaminophenoxy)propane; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; biphenyl-2,4,4'-triamine hydrochloride; 5-(4-amino-phenyl)aminomethyl-benzene-1,3-diamine hydrochloride; 5-phenylaminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenylamino)-methyl]-phenol hydrochloride; 4-amino-2-propylaminomethyl-phenol; N-benzo[1,3]di-oxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide; 4-amino-2-(isopropylamino-methyl)-phenol; 4-thiophen-3-yl-benzene-1,3-diamine; 5-phenylaminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl) aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-di-amino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethylamino)-2-methyl-phenol; 5-amino-2,4-dichloro-phenol; 3-amino-2-methyl-phenol; 3-amino-2,6-dimethyl-phenol; 3-amino-2-chloro-6-methyl-phenol; 5-amino-2-(2-hydroxy-ethoxy)-phenol; 2-chloro-5-(2,2,2-trifluoro-ethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethylamino)phenol; 3-(diethylamino)phenol; 5-amino-4-fluoro-2-methylphenol; 5-amino-4-ethoxy-2-methylphenol; 3-amino-2,4-dichloro-phenol; 3-[(2-methoxyethyl)amino]phenol; 3-[(2-hydroxyethyl)amino]phenol; 5-amino-2-ethyl-phenol; 5-amino-2-methoxyphenol; 5-[(3-hydroxy-propyl)amino]-2-methylphenol; 3-[(3-hydroxy-2-methylphenyl)-amino]propane-1,2-diol; 3-[(2-hydroxyethyl)amino]-2-methylphenol; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; 5-cyclobutylamino-2-methyl-phenol 1-methyl-2-hydroxy-4-(2'-hydroxyethyl)amino-benzene; and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxy-ethoxy)-pyridin-2-yl]oxy}-ethanol; 1H-indol-4-ol; 5-amino-2,6-dimethoxypyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxypyridine-2,6-diamine; 6-methoxypyridine-2,3-diamine; 3,4-dihydro-2H-1,4-benzoxazin-6-amine; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methylpyrazolo[5,1-e]-1,2,3-triazole; 5-methyl-6-chloropyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one; 6-hydroxybenzomorpholine; and 3-amino-2-methylamino-6-methoxypyridine; salts thereof; and mixtures thereof.

In some embodiments, couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof; m-phenylenediamine derivatives such as: benzene-1,3-diamine; 2-(2,4-diamino-phenoxy)-ethanol; 4-{3-[(2,4-diaminophenyl)oxy]propoxy}benzene-1,3-diamine; 2-(3-amino-4-methoxy-phenylamino)-ethanol; 2-[2,4-diamino-5-(2-hydroxy-ethoxy)-phenoxy]-ethanol; and 3-(2,4-diaminophenoxy)-propan-1-ol; 2,4-diamino-5-(2'-hydroxyethyloxy) toluene; N,N-dimethyl-3-ureidoaniline; 2,4-diamino-5- fluorotoluene; 1-methyl-2,6-bis(2-hydroxyethylamino) benzene; and mixtures thereof; m-aminophenol derivatives such as: 3-aminophenol; 5-amino-2-methyl-phenol; 3-amino-2,6-dimethylphenol; 5-(2-hydroxy-ethylamino)-2-methyl-phenol; and 3-amino-2-methyl-phenol; 1-hydroxy-3-amino-2,4-dichlorobenzene; 1,3-bis-(2,4-diaminophenoxy) propane; 1-hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; salts thereof; and mixtures thereof.

In certain embodiments, couplers include: 2-amino-5-ethyl-phenol; benzene-1,3-diol; 4-chlorobenzene-1,3-diol; 4,6-dichlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxyethanol; 4-amino-2-hydroxyphenoxyethanol; 1-naphthol; 2-methyl-naphthol; 3-aminophenol; 3-amino-2-methylphenol; 4-hydroxy-1,2-methylenedioxybenzene; 4-amino-1,2-methylenedioxybenzene; 4-(2'-hydroxyethyl)amino-1,2-methylenedioxybenzene; 1-Methyl-2-hydroxy-4-(2'-hydroxyethyl) aminobenzene; 2,4-diaminophenetole; 2,4-diamino-5-methylphenetole; 4-hydroxyindole; 3-amino-5-hydroxy-2,6-dimethoxypyridine; and 3,5-diamino-2,6-dimethoxypyridine; benzene-1,3-diamine; 2-aminopyridin-3-ol; 1-phenyl-3-methylpyrazol-5-one; salts thereof; and mixtures thereof.

Additionally, in some embodiments, developers and couplers include 5-methoxymethyl-2-aminophenol; 5-ethyl-2-aminophenol; 5-phenyl-2-aminophenol; 5-cyanoethyl-2-aminophenol; salts thereof; and mixtures thereof.

The hair dye compositions of the present invention may also include non oxidative dyes, or direct dyes, which are suitable for delivering shade modification or highlights. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene)methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono) methyl]-pyridinium, methyl sulfate; 2-[(4-aminophenyl) azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; N,N-dimethyl-3-((4-(methylamino)-9,10-dioxo-9,10-dihydroanthracen-1-yl)amino)-N-propylpropan-1-aminium bromide, HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

The hair dye compositions of the present invention will generally comprise from about 0.001% to about 10% of dyes upon admixture of the powder composition with water. For example, compositions providing low intensity dyeing such as natural blonde to light brown hair shades generally comprise from about 0.001% to about 5%, preferably from about 0.1% to about 2%, more preferably from about 0.2% to about 1% by weight of precursors and couplers upon admixture with water. Darker shades such as browns and black typically comprise from 0.001% to about 10% by weight, preferably from about 0.05% to about 7% by weight, more preferably form about 1% to about 5% of precursors and couplers.

Surfactants

The compositions according to the present invention may further comprise one or more surfactants for providing feel benefits, such as smoothness. Surfactants suitable for use herein generally have a lipophilic chain length of from about 8 to about 30 carbon atoms and can be selected from anionic, nonionic, amphoteric and cationic surfactants and mixtures thereof. Preferred surfactants include non-ionic surfactants comprising one or more polyethyleneoxide chain, for example polyoxyethylene alkyl ethers or polyethyleneglycol fatty acid esters. Another preferred surfactants are alkyl ether sulphates or alkyl ether phosphates, where particularly preferable are alkyl ether phosphates having 1-20, preferably 1-10 and most preferably 1-5 ethylene oxide units.

Any combination of surfactants can be used. The surfactants will generally be used at levels of from about 0.05% to about 30% by weight of the composition, preferably of from about 0.1% to about 15%, more preferably of from about 0.2% to about 10%.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage prevention benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant.

Method of Use

It is understood that the examples of methods of use and embodiments described herein are for illustrative purposes only and that various modifications or changes in light thereof will be suggested to one skilled in the art without departing from the scope of the present invention. The powder composition of the present invention is provided in hermetically sealed packages in an amount suitable for single usage. During its shelf life and, the composition must be stable from reaction of the components therein, as well as atmospheric humidity. The present composition is supplied with instructions for the consumer to mix the appropriate amount of water per single use dosage of powdered composition to provide the target concentration of components. The amount of components in the powder composition of the present invention, therefore, is adjusted according to the prescribed amount of water with which the powder composition is to be admixed. Typically, the powder composition is designed to mix with from about 4 to about 5 times weight of water.

In that the admixing with water is typically conducted at the consumer's home with mild manual mixing, the reaction and thickening of the dispersed composition is so designed to proceed with mild mechanical mixing within about 60 seconds, more preferably within about 30 seconds. The consumer mixes the composition with water immediately before use and applies it onto the hair.

After working the obtained dispersed composition through the region of hair to dye for a few minutes (to insure uniform application to all of the hair), the composition is allowed to remain on the hair for an amount sufficient for the dyeing to take place (usually from about 2 to 60 minutes, typically about 30 to 45 minutes). The consumer then rinses his/her hair thoroughly with tap water and allows it to dry. It is observed that the hair has changed from its original color to the desired color.

The present invention also includes embodiments wherein the method of coloring or bleaching hair comprises applying a composition comprising at least one oxidising agent, at least one source of carbonate, carbamate, or hydrogen carbonate ions and mixtures thereof, and a polymer thickening system as defined herein free of radical scavengers, the composition having a pH of up to about 9.4, for at least about 50% of the time period the composition is applied to the hair.

According to the present invention the methods of coloring or bleaching hair also comprise embodiments whereby the composition is applied to the hair and preferably the mixture is worked for a few minutes (to insure uniform application to all of the hair). The composition is then allowed to remain on the hair in order for the color to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual. This method provides additional convenience to consumer by permitting faster coloring or bleaching application.

According to an alternative embodiment of the present invention, the method of coloring and or bleaching the hair is a sequential oxidative hair coloring or hair bleaching method comprising the steps of at least two sequential oxidative hair color or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes. This method allows consumer to perform coloring or bleaching process in a way similar to conventional hair washing or conditioning process.

The composition herein can be manufactured economically utilizing any one of the standard approaches. The composition may be provided in structured packages, packets, or sachets, so long as they are made of air impermeable material and remain hermetically sealed for the desired shelf life. Air remaining in the package may be vacuumed or replaced with inert gas such as nitrogen before sealing.

The application of the dispersed composition to the hair may be conducted with devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

Examples

The following examples illustrate oxidative dye compositions according to the present invention. It is understood that the examples and embodiments described herein are for illustrative purposes only and that various modifications or changes in light thereof will be suggested to one skilled in the art without departing from the scope of the present invention. Examples 1-29 are compositions according to the present invention, while Comparative Examples 1-5 are those that are not according to the present invention.

Compositions and Color Results for Examples 1-28

Examples 1-28 are powder hair coloring compositions of the present invention. The components for compositions and color results for Examples 1-28 are listed in Tables 1-7 below, followed by the method of making them, and method us using them.

TABLE 1

| Components (%) | 1 | 2 | 3 | 4 |
|---|---|---|---|---|
| Sodium Percarbonate | 46.07 | 46.07 | 46.07 | 46.06 |
| Ammonium Sulfate | 27.18 | 27.18 | 27.18 | 27.18 |
| Sodium Glycine Salt | 9.67 | 9.67 | 9.67 | 9.67 |
| Acrylates/C10-30 Alkyl Acrylate Crosspolymer* | 9.60 | 9.60 | 9.60 | 9.60 |
| p-phenylenediamine | 1.38 | 1.07 | 0.71 | 0.36 |
| N,N-Bis-(2-hydroxyethyl)-p-phenylenediamine sulfate | 0.69 | 0.69 | 0.69 | 0.69 |
| Resorcinol | 1.17 | 1.17 | 1.17 | 1.17 |
| p-aminophenol | 2.21 | 2.52 | 2.88 | 3.24 |
| 4-amino-2-hydroxytoluene | 1.37 | 1.37 | 1.37 | 1.37 |
| 2-Methylresorcinol | 0.28 | 0.28 | 0.28 | 0.28 |
| Phenyl Methyl Pyrazolone | 0.38 | 0.38 | 0.38 | 0.38 |
| Result: | Medium Brown | Medium Brown | Medium Brown | Medium Brown |

TABLE 2

| Components (%) | 5 | 6 | 7 | 8 |
|---|---|---|---|---|
| Sodium Percarbonate | 46.07 | 46.07 | 45.44 | 44.25 |
| Ammonium Sulfate | 27.18 | 27.18 | 26.81 | 26.11 |
| Sodium Glycine Salt | 9.68 | 9.68 | 9.54 | 9.29 |
| Acrylates/C10-30 Alkyl Acrylate Crosspolymer | 9.60 | 9.60 | 9.47 | 9.22 |
| p-phenylenediamine | 1.78 | 2.14 | 1.36 | 1.32 |
| N,N-Bis-(2-hydroxyethyl)-p-phenylenediamine sulfate | 0.69 | 0.69 | 0.68 | 0.66 |
| Resorcinol | 1.17 | 1.17 | 1.16 | 1.13 |
| p-aminophenol | 1.80 | 1.44 | 2.18 | 2.12 |
| 4-amino-2-hydroxytoluene | 1.37 | 1.37 | 2.70 | 5.26 |
| 2-Methylresorcinol | 0.28 | 0.28 | 0.27 | 0.27 |
| Phenyl Methyl Pyrazolone | 0.38 | 0.38 | 0.38 | 0.37 |
| Result: | Medium Brown | Medium Brown | Medium Red-Brown | Light Red-Brown |

TABLE 3

| Component (%) | 9 | 10 | 11 | 12 |
|---|---|---|---|---|
| Sodium Percarbonate | 45.71 | 44.63 | 44.29 | 44.26 |
| Ammonium Sulfate | 26.97 | 26.33 | 26.13 | 26.11 |
| Sodium Glycine Salt | 9.60 | 9.37 | 9.30 | 9.29 |
| Acrylates/C10-30 Alkyl Acrylate Crosspolymer | 9.52 | 9.30 | 9.23 | 9.22 |
| p-phenylenediamine | 1.37 | 1.34 | 1.66 | 2.07 |
| N,N-Bis-(2-hydroxyethyl)-p-phenylenediamine sulfate | 0.69 | 0.67 | 0.66 | 0.66 |
| Resorcinol (%) | 0.58 | 0.28 | 1.13 | 1.13 |
| p-aminophenol | 2.19 | 2.14 | 1.70 | 1.36 |
| 4-amino-2-hydroxytoluene | 2.72 | 5.30 | 5.26 | 5.26 |
| 2-Methylresorcinol | 0.27 | 0.27 | 0.27 | 0.27 |
| Phenyl Methyl Pyrazolone | 0.38 | 0.38 | 0.37 | 0.37 |
| Result: | Red-Brown | Medium Auburn | Medium Auburn | Dark Auburn |

TABLE 4

| Component (%) | 13 | 14 | 15 | 16 |
|---|---|---|---|---|
| Sodium Percarbonate | 44.15 | 43.96 | 43.69 | 43.31 |
| Ammonium Sulfate | 26.05 | 25.94 | 25.77 | 25.56 |
| Sodium Glycine Salt | 9.27 | 9.23 | 9.17 | 9.10 |
| Acrylates/C10-30 Alkyl Acrylate Crosspolymer* | 9.20 | 9.16 | 9.10 | 9.02 |
| p-phenylenediamine | 2.58 | 3.21 | 3.99 | 4.95 |
| N,N-Bis-(2-hydroxyethyl)-p-phenylenediamine sulfate | 0.66 | 0.66 | 0.66 | 0.65 |
| Resorcinol (%) | 1.13 | 1.12 | 1.11 | 1.10 |
| p-aminophenol | 1.08 | 0.86 | 0.69 | 0.55 |
| 4-amino-2-hydroxytoluene | 5.25 | 5.22 | 5.19 | 5.15 |
| 2-Methylresorcinol | 0.26 | 0.26 | 0.26 | 0.26 |
| Phenyl Methyl Pyrazolone | 0.37 | 0.37 | 0.36 | 0.36 |
| Result: | Dark Auburn | Dark Auburn | Dark Auburn | Dark Auburn |

TABLE 5

| Components (%) | 17 | 18 | 19 | 20 |
|---|---|---|---|---|
| Sodium Percarbonate | 43.22 | 43.22 | 43.25 | 43.26 |
| Ammonium Sulfate | 25.50 | 25.50 | 25.52 | 25.52 |
| Sodium Glycine Salt | 9.08 | 9.08 | 9.08 | 9.08 |
| Acrylates/C10-30 Alkyl Acrylate Crosspolymer* | 9.00 | 9.00 | 9.01 | 9.01 |
| p-phenylenediamine | 2.16 | 2.16 | 2.16 | 2.16 |
| 1-Naphthol | 0.01 | 0.01 | 0.00 | 0.00 |
| N,N-Bis-(2-hydroxyethyl)-p-phenylenediamine sulfate | 0.02 | 0.02 | 0.02 | 0.02 |
| Resorcinol (%) | 0.11 | 0.11 | 0.05 | 0.03 |
| p-aminophenol | 0.01 | 0.01 | 0.01 | 0.01 |
| 4-amino-2-hydroxytoluene | 0.04 | 0.04 | 0.04 | 0.04 |
| 2-Methylresorcinol | 8.31 | 8.31 | 8.32 | 8.32 |
| Phenyl Methyl Pyrazolone | 2.55 | 2.55 | 2.55 | 2.55 |
| Result: | Dark Brown | Dark Brown | Dark Brown | Dark Brown |

TABLE 6

| Components (%) | 21 | 22 | 23 | 24 |
|---|---|---|---|---|
| Sodium Percarbonate | 43.25 | 43.26 | 43.02 | 42.91 |
| Ammonium Sulfate | 25.52 | 25.52 | 25.38 | 25.32 |
| Sodium Glycine Salt | 9.08 | 9.08 | 9.04 | 9.01 |
| Acrylates/C10-30 Alkyl Acrylate Crosspolymer | 9.01 | 9.01 | 8.96 | 8.94 |
| p-phenylenediamine | 2.16 | 2.16 | 2.26 | 2.25 |
| 1-Naphthol | 0.01 | 0.01 | 0.27 | 0.54 |
| N,N-Bis-(2-hydroxyethyl)-p-phenylenediamine sulfate | 0.02 | 0.02 | 0.12 | 0.12 |
| Resorcinol | 0.05 | 0.03 | 0.09 | 0.09 |
| p-aminophenol | 0.01 | 0.01 | 0.00 | 0.00 |
| 4-amino-2-hydroxytoluene | 0.04 | 0.04 | 0.04 | 0.04 |
| 2-Methylresorcinol | 8.32 | 8.32 | 8.28 | 8.25 |
| Phenyl Methyl Pyrazolone | 2.55 | 2.55 | 2.54 | 2.53 |
| Result: | Dark Brown | Dark Brown | Black-Brown | Black-Brown |

TABLE 7

| Components (%) | 25 | 26 | 27 | 28 |
|---|---|---|---|---|
| Sodium Percarbonate | 43.10 | 43.11 | 43.04 | 42.94 |
| Ammonium Sulfate | 25.43 | 25.44 | 25.40 | 25.33 |
| Sodium Glycine Salt | 9.05 | 9.05 | 9.04 | 9.02 |
| Acrylates/C10-30 Alkyl Acrylate Crosspolymer | 8.98 | 8.98 | 8.97 | 8.95 |
| p-phenylenediamine | 2.26 | 2.26 | 2.26 | 2.25 |
| 1-Naphthol | 0.14 | 0.14 | 0.27 | 0.54 |
| N,N-Bis-(2-hydroxyethyl)-p-phenylenediamine sulfate | 0.12 | 0.12 | 0.12 | 0.12 |

TABLE 7-continued

| Components (%) | 25 | 26 | 27 | 28 |
| --- | --- | --- | --- | --- |
| Resorcinol (%) | 0.05 | 0.02 | 0.05 | 0.02 |
| 4-amino-2-hydroxytoluene | 0.04 | 0.04 | 0.04 | 0.04 |
| 2-Methylresorcinol | 8.29 | 8.29 | 8.28 | 8.26 |
| Phenyl Methyl Pyrazolone | 2.54 | 2.54 | 2.54 | 2.53 |
| Result: | Black-Brown | Black-Brown | Black-Brown | Black-Brown |

*Acrylates/C10-30 Alkyl Acrylate Crosspolymer: Carbopol ETD 2020 available from Noveon The compositions of the present invention are capable of providing a variety of shades.

Method of Making

The components are mixed thoroughly, transferred to a packaging made of air impermeable material in a nitrogen atmosphere, and sealed. Instructions are provided to mix contents of each dosage with 4 times weight of water.

Method of Use and Hair Color Result

The composition is manually mixed with 4 times weight of water for 60 seconds, then applied to the hair to be left for 30 minutes, and washed off from the hair with water. When applied to the hair according to such instructions, each composition provided hair color indicated "Result". The present composition is capable of providing various hair color results, and thus has the potential of providing a broad variety of shades.

Gray Hair Coverage

Example 1 described above and Comparative Example 1, not according to the present invention, were subject to testing effectiveness of gray hair coverage. Comparative Example 1 is Bigen Xpressive Café Latte available in the United States in 2007, having a similar shade to Example 1.

The following hair switches were dyed with Example 1 and Comparative Example 1 each, according to the method of use as described above, albeit Comparative Example 1 was added to 100 ml of water, per instructions provided on the package.
1) 3/0 dark brown hair
2) A 50/50 blend of gray and 3/0 hair After dyeing, the experimental hair switches along with an undyed 50% gray-3/0 hair switch were washed under the following conditions:

35-40° C. water with a flow-rate of 4±0.5 l/min
    Shampooed once with Pantene Clarifying Shampoo available in the United States in 2007
    Rinsed
    Dried with an electric blow drier.

After drying, L, a, b values were obtained for the dyed 3/0, dyed 50% gray blend, and undyed 50% gray blend hair using a Minolta Spectrophotometer CM-3700d. L, a, b values were then used to calculate $\Delta E$ values using the equation $\Delta E = \sqrt{(L^2 + a^2 + b^2)}$. From these values, the percentage of gray coverage was calculated as follows:

$$\% \text{ gray coverage} = \left(\frac{\Delta E_{dyedgray}}{(\Delta E_{dyed\ 3/0} - \Delta E_{undyedgray})}\right) * 100$$

The Gray Hair Coverage obtained for Example 1 and Comparative Example 1 were as such.

| | Example 1 | Comparative Example 1 |
| --- | --- | --- |
| Gray Hair Coverage (%) | 82.5% | 31.4% |

As can be understood from the results, the composition of the present invention of similar shade provided significantly better gray hair dyeing compared to Comparative Example 1.

Thickener Properties and pH

Example 29 according to the present invention, and Comparative Examples 1-5, not according to the present invention, were subject to testing properties as a thickener. Examples 29 and Comparative Examples 1-5 lack hair dyes for easy observation of the thickening properties. Table 9 shows the base composition for all of Example 29 and Comparative Examples 1-5. To this base composition was added specific thickeners as specified in Table 10.

TABLE 9

| Components | Parts by weight |
| --- | --- |
| Sodium percarbonate | 12.00 |
| Ammonium sulfate | 7.08 |
| Sodium glycine salt | 2.52 |

TABLE 10

| Example number | Description of thickener |
| --- | --- |
| Example 29 | Acrylates/C10-30 Alkyl Acrylate Crosspolymer: Carbopol ETD 2020 available from Noveon |
| Comparative Example 1 | PEG 15 stearate: Aculyn 60 available from Rohm & Haas |
| Comparative Example 2 | Carboxymethyl cellulose 700k, 0.9DS *1) |
| Comparative Example 3 | Carboxymethyl cellulose 250k, 0.7DS |
| Comparative Example 4 | Carboxymethyl cellulose 250k, 0.9DS |
| Comparative Example 5 | Carboxymethyl cellulose 250k, 1.2DS |

*1) k stands for weight average molecular weight, DS stands for degree of substitution.

Each composition was admixed with 4.17 times weight of water, providing a dispersed composition having 2.44% of thickener, respectively. Upon admixing with water, each composition was stirred with a mixing rod, and observed of the time to reach maximum thickness, and further observed if clumping occurred. After reaching maximum thickness, the dispersed composition was tested as to adhesion on the hair and spreadability on the hair by an expert panelist. For only those dispersed compositions having adequate adhesion and spreadability, the viscosity was measured at 0.5 rpm using Brookfield viscometer spindle S52. The pH was measured for all dispersed compositions, except Comparative Example 1, which was too thick for measuring pH. The results for each thickener property items were as specified in Table 11.

TABLE 11

| | Time to Maximum Thickness (seconds) | Clumping | Adhesion to Hair | Spreadability on Hair | Viscosity (mPas) | pH |
| --- | --- | --- | --- | --- | --- | --- |
| Example 29 | 30 | No | Pass | Pass | 13500 | 9.25 |
| Comparative Example 1 | | Yes | Pass | Fail | | |
| Comparative Example 2 | 140 | Yes | Fail | Pass | | 9.57 |
| Comparative Example 3 | 151 | Yes | Fail | Pass | | 9.55 |

TABLE 11-continued

| | Time to Maximum Thickness (seconds) | Clumping | Adhesion to Hair | Spreadability on Hair | Viscosity (mPas) | pH |
|---|---|---|---|---|---|---|
| Comparative Example 4 | 137 | Yes | Fail | Pass | | 9.62 |
| Comparative Example 5 | 110 | No | Fail | Pass | | 9.67 |

As can be understood from the results above, only Example 29 of the present invention provided satisfactory thickener properties, as well as appropriate pH.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A powder hair coloring or bleaching composition comprising:
    a) at least one solid source of carbonate ions, carbamate ions, hydrogencarbonate ions, or mixtures thereof;
    b) at least one solid source of oxidizing agent;
    c) at least one solid source of ammonium ions; and
    d) a crosslinked carboxylic acid polymer thickener having a particle size of no more than about 10 microns in an amount which, upon admixture of the powder composition with water to provide a concentration of from about 1% to about 3%, provides the dispersed composition a viscosity of from about 10000 mPas to about 20000 mPas when measured at 0.5 rpm using Brookfield viscometer spindle S52, and a pH of from about 8.5 to about 9.4.

2. The composition of claim 1 wherein said crosslinked carboxylic acid polymer thickener is a C10 to C30 alkyl acrylate crosspolymer.

3. The composition of claim 1 wherein upon admixture with water the composition generates peroxymonocarbonate ions.

4. The composition of claim 1 wherein the solid source of carbonate ions, carbamate ions, hydrogencarbonate ions, or mixtures thereof is a percarbonate salt.

5. The composition of claim 4 wherein the percarbonate salt is selected from the group consisting of sodium percarbonate, potassium percarbonate, and calcium percarbonate.

6. The composition of claim 1 wherein the solid source of ammonium ions is selected from the group consisting of ammonium chloride, ammonium sulfate, ammonium nitrate, ammonium phosphate, ammonium acetate, ammonium carbonate, ammonium hydrogen carbonate, ammonium carbamate, and ammonium hydroxide.

7. The composition of claim 6 wherein the solid source of ammonium ions is ammonium sulfate.

8. The composition of claim 1 further comprising a radical scavenger.

9. The composition of claim 8 wherein the radical scavenger is selected from the group consisting of alkanol amines and amino acids having an energy of reaction from about 0 kcal/mol to 14 kcal/mol, and a molecular weight of no greater than about 250.

10. The composition of claim 9 wherein the radical scavenger is selected from the group consisting of glucosamine, glycine, glutamic acid, arginine, lysine, glutamine, histidine, serine, and mixtures thereof.

11. The composition of claim 1 further comprising a chelant.

12. A method of coloring or bleaching the hair comprising the steps of:
    a) providing the composition of claim 1;
    b) admixing the composition with a prescribed amount of water;
    c) applying the dispersed composition to the hair;
    d) allowing the dispersed composition to remain on the hair for from about 2 to about 60 minutes; and
    e) rinsing the dispersed composition from the hair.

* * * * *